(12) United States Patent
Bennett

(10) Patent No.: US 10,492,796 B2
(45) Date of Patent: Dec. 3, 2019

(54) TOURNIQUET HAVING A BUCKLE RESISTANT TO TORSIONAL FORCE

(71) Applicant: Composite Resources, Inc., Rock Hill, SC (US)

(72) Inventor: Jonathan Peter Bennett, Rock Hill, SC (US)

(73) Assignee: Composite Resources, Inc., Rock Hill, SC (US)

( * ) Notice: Subject to any disclaimer, the term of this patent is extended or adjusted under 35 U.S.C. 154(b) by 185 days.

(21) Appl. No.: 15/579,716

(22) PCT Filed: Oct. 6, 2017

(86) PCT No.: PCT/US2017/055471
§ 371 (c)(1),
(2) Date: Dec. 5, 2017

(87) PCT Pub. No.: WO2018/071286
PCT Pub. Date: Apr. 19, 2018

(65) Prior Publication Data
US 2019/0223884 A1    Jul. 25, 2019

Related U.S. Application Data

(60) Provisional application No. 62/407,370, filed on Oct. 12, 2016.

(51) Int. Cl.
*A61B 17/132* (2006.01)
(52) U.S. Cl.
CPC ................................ *A61B 17/1327* (2013.01)

(58) Field of Classification Search
CPC .............. A61B 17/1327; A61B 17/132; A61B 17/1322; A61B 17/1325; A44B 11/00; A44B 11/065; A44B 11/02; A44B 11/22
See application file for complete search history.

(56) References Cited

U.S. PATENT DOCUMENTS

| | | |
|---|---|---|
| 2008/0022161 A1 | 9/2008 | Rose |
| 2008/0221612 A1 | 9/2008 | Rose |
| 2009/0006284 A1 | 3/2009 | Esposito et al. |
| 2009/0062842 A1* | 3/2009 | Esposito ............ A61B 17/1327 606/203 |
| 2010/0002183 A1 | 9/2010 | Mamie |
| 2010/0218348 A1 | 9/2010 | Mamie |
| 2011/0017854 A1 | 7/2011 | Johnson et al. |

(Continued)

*Primary Examiner* — Katherine M Rodjom
(74) *Attorney, Agent, or Firm* — Nexsen Pruet, LLC; Michael A. Mann

(57) ABSTRACT

A tourniquet having a first elongated member with a buckle on one end, and a second elongated member attached at both ends to the end of the first elongated member but leaving an intermediate portion of the second elongated member otherwise slidable with respect to the first elongated member. A windlass is used to twist the intermediate portion to apply tension to the first longitudinal member. Twisting the windlass produces a lineal component to the force and a torsional component. The buckle includes a first lateral side, a second lateral side and an intermediate bar between and spaced apart from them. The buckle also includes an anti-torsional plate that resists the torsional force. The buckle also has "teeth" the resist movement of the first longitudinal member from the buckle.

15 Claims, 6 Drawing Sheets

(56) References Cited

U.S. PATENT DOCUMENTS

2011/0178546 A1    7/2011   Johnson et al.
2012/0071917 A1*   3/2012   McDonald ......... A61B 17/1322
                                                                                        606/203
2015/0107067 A1    4/2015   Hede et al.

\* cited by examiner

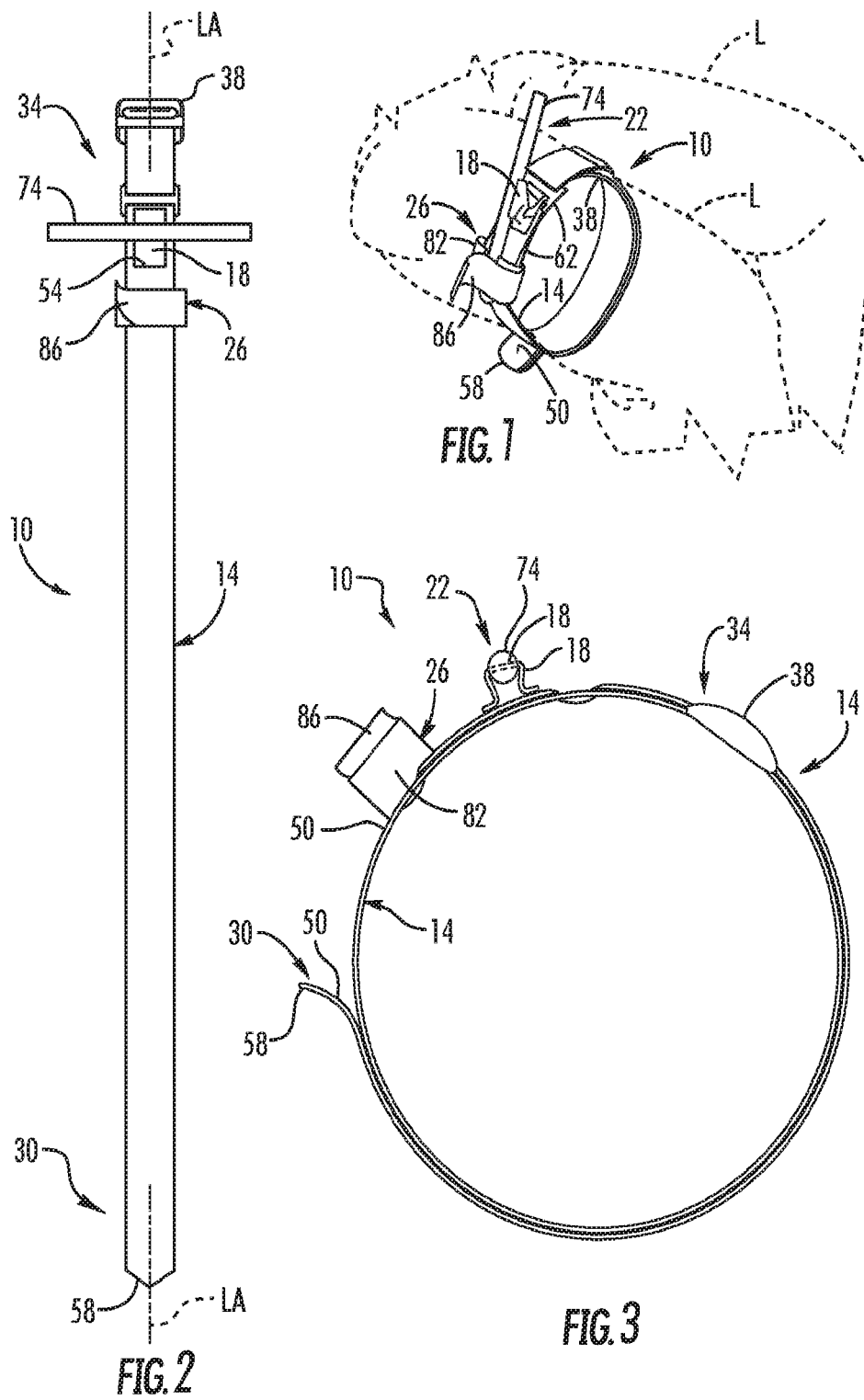

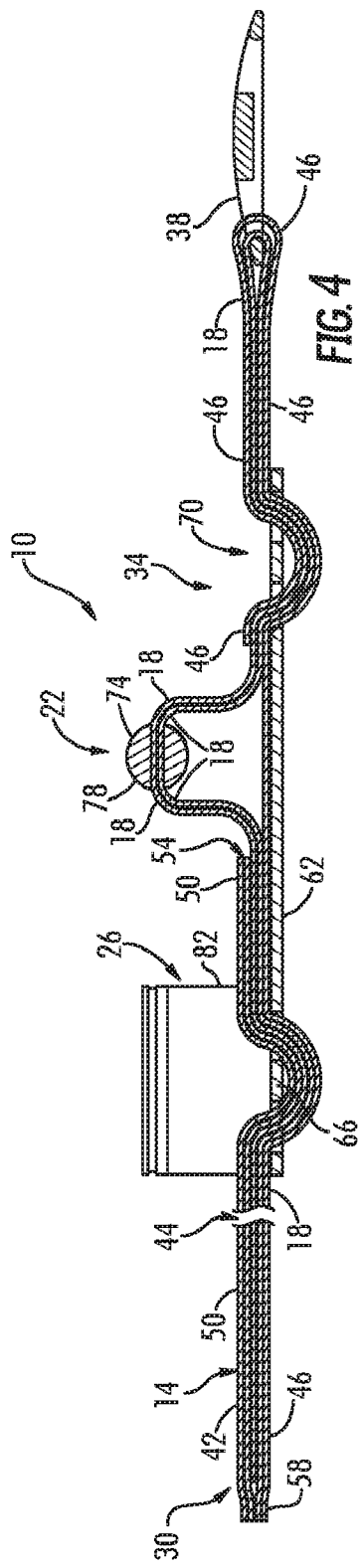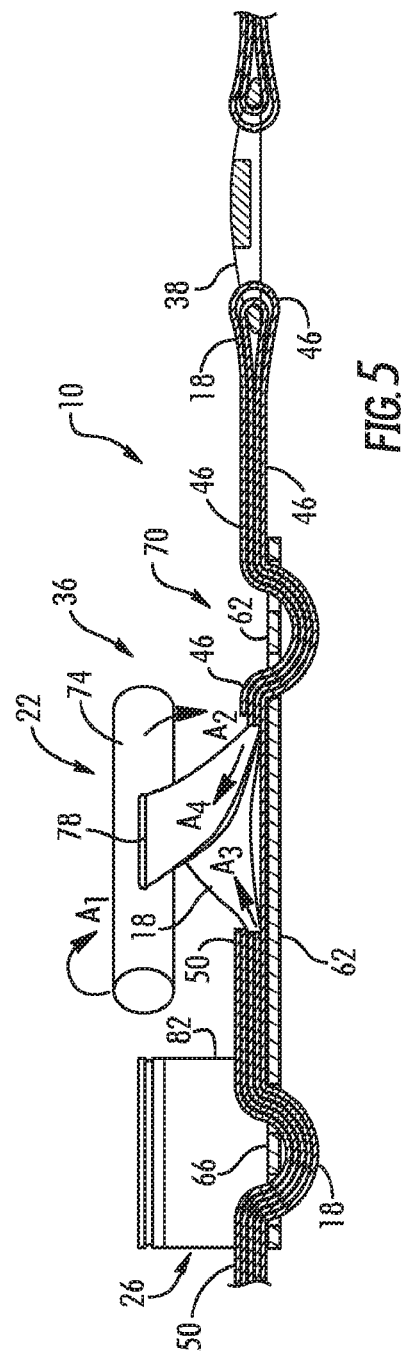

TOURNIQUET HAVING A BUCKLE RESISTANT TO TORSIONAL FORCE

CROSS REFERENCE TO RELATED APPLICATIONS

This application is a 35 U.S.C. § 371 U.S. national phase entry of International Application No. PCT/US2017/055471 having an international filing date of Oct. 6, 2017, which claims the benefit of U.S. Provisional Patent Application No. 62/407,370 filed Oct. 12, 2016, each of which is incorporated herein by reference in its entirety.

CROSS-REFERENCE TO RELATED APPLICATIONS

The presently disclosed subject matter is related to and claims priority to U.S. Provisional Patent Application No. 62/407,370 entitled "Tourniquet Having A Buckle Resistant To Torsional Forces" filed on Oct. 12, 2016, the entire disclosure of which is incorporated herein by reference.

FIELD OF TECHNOLOGY

The present disclosure relates to tourniquets and, more particularly, to tourniquet resistant to torsional forces.

BACKGROUND

When an injured person is alone or medical assistance is not immediately available, loss of blood is a major risk of death. The use of a tourniquet to stop blood loss from an injured arm or limb is well known. Without help and bleeding profusely, the injured victim must be able to apply a tourniquet to his or her own arm or limb using only one hand to have a chance at survival.

Tourniquets of the prior art comprise an elongated strap and a buckle and another component intended to increase circumferential pressure on the limb, such as a ratchet to windlass. The ratchet and windlass generate inward radial compression when the tourniquet is wrapped around the injured limb by using high levels of circumferential tension. As the pressure on the limb increases, the friction between the tourniquet and the limb also increases, causing the underlying soft tissue to move with the strap as it is drawn tighter. Soft tissues underlying the strap may be drawn into the buckle where the soft tissue may be pinched by the very highly localized pressure against it. Shearing forces may also endanger the soft tissue, increasing the probability of nerve damage and tearing. Friction between the strap and the limb may also create regions of low pressure where tension is not evenly distributed by the strap around the limb's circumference, and, as a result, arterial blood may not be completely staunched despite high tension on the strap.

In general, the application of uneven pressure around the limb may drive overall tourniquet pressures ever higher to stop arterial blood flow, while also increasing the probability of a range of injuries to nerves, muscles, and limbs.

Those engaged in activities where the risk of serious injury is heightened, including many recreational activities, such as hiking, rock climbing, and camping, will select the gear they take with them based on various criteria, including weight. Simply stated, if a tourniquet is too bulky or has an excessive weight, the potential user will not pack and carry a tourniquet. A small, lightweight tourniquet that can be easily packed and carried is more likely to be included as part of recreational gear.

Accordingly, there is a need for an easy to use, lightweight tourniquet that effectively restricts blood flow, and that ideally can be applied with one hand, without pinching, tearing, or otherwise damaging soft tissues.

SUMMARY

According to its major aspects and briefly recited, herein is disclosed a tourniquet having a first elongated member with a first end and an opposing second end. A buckle is attached to the first end. The present tourniquet has second elongated member with a first end and an opposing second end. The first end and the second end of the second elongated member are attached to the second end of the first elongated member with leaving an intermediate portion of the second elongated member between the attached first and second ends of the second elongated member otherwise slidable with respect to said first elongated member. A windlass is configured to apply force to said intermediate portion of the second longitudinal member when it is operated. That force has a lineal component and a torsional component.

The buckle is a feature of the disclosure. The buckle has a first lateral side with a first lateral sidewall, a second lateral side and an intermediate bar located between them and spaced apart from them. The first lateral sidewall has a first lateral side; the second lateral sidewall has a second lateral side. An anti-torsion plate, which may be in the form of a rectangle, is attached to the first lateral sidewall. The second lateral side may have one or more teeth projecting toward the intermediate bar. The second end of the first elongated member runs between the first lateral side and the intermediate bar to define a loop in the second end of the first elongated member. The anti-torsion plate resists the torsional component of the force on the loop when the windlass applies force.

The anti-torsion plate, another feature of the disclosure, may have a side, and the loop in the second end of the first elongated member encircles the anti-torsion plate when it run between the intermediate bar and the first lateral side to form the loop. The torsion plate may be rectangular so a first side of torsion plate can be attached to the first lateral sidewall of the first lateral side of the buckle, and the loop is attached to a second side and a third side of said rectangular of said anti-torsion plate.

A feature of the present tourniquet is a base. The first elongated member is attached to the base so that, when the windlass applies a force to the second elongated member, the ends of the second elongated member are drawn toward the base.

Those skilled in the art of tourniquets and their use will see additional features and their advantages from a careful review of the Detail Description, accompanied by the drawings.

BRIEF DESCRIPTION OF THE DRAWINGS

In the figures:

FIG. 1 is a right-side perspective view of the tourniquet applied to a person's right limb (as shown in dashed lines);

FIG. 2 is a plan view of the device shown in FIG. 1, where the device is stretched out along its longitudinal axis;

FIG. 3 is a right elevation of the device shown in FIG. 1, where the device is shown prior to tightening the device using the windlass;

FIG. 4 is a cross-sectional view of the device shown in FIG. 2 with the windlass in an unwound position;

FIG. 5 is the same cross-sectional view of the device as shown in FIG. 4 but with the first elongated member looped through the buckle and the windlass in a partially wound position;

DETAILED DESCRIPTION

Figure 6:
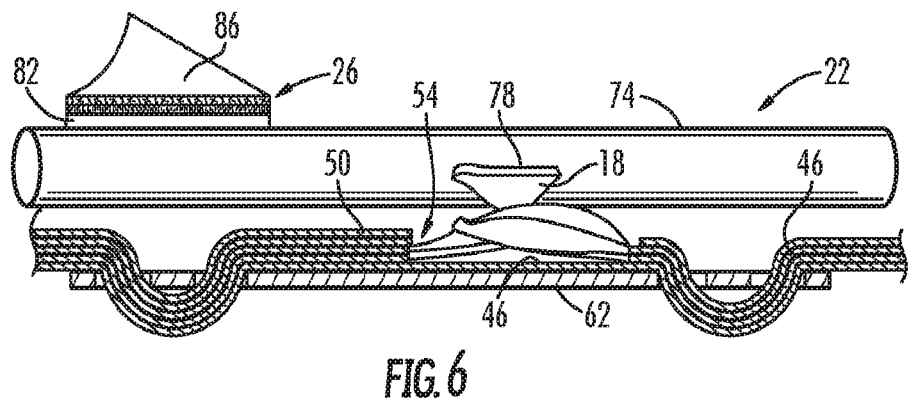
FIG. 6 is a cross-sectional view of a portion of the device with the windlass in a wound position.

Herein is described a tourniquet that resists torsional forces of the windlass while permitting linear forces when the tourniquet is tightened. Furthermore, the tourniquet is less likely to slip or to pull skin into the buckle where it may be pinched and injured. Moreover, the tourniquet can be operated with one hand, thereby allowing the user to apply the tourniquet unassisted.

Referring now to FIG. 1, a tourniquet 10 is shown in accordance with the present disclosure. The tourniquet 10 comprises a first elongated member 14, a second elongated member 18, a tension mechanism 22, and a securing mechanism 26. As shown in FIG. 1, the tourniquet 10 can be applied to an appendage L, such as a leg, and then tightened to restrict the flow of blood to Limb L.

Referring now to FIG. 2, the tourniquet 10 is shown prior to use and in a stretched-out orientation. First elongated member 14 comprises a longitudinally extensive material having a first end 30 and a second end 34. In accordance with the present disclosure, second end 34 includes a restraining mechanism, such as a ring or buckle 38.

When the tourniquet 10 is applied to limb L such as shown in FIG. 1, first end 30 is looped through buckle 38 and pulled tight around limb L, thus providing means for circumferentially surrounding or encircling limb L. FIG. 3 depicts tourniquet 10 after first end 30 is looped through buckle 38.

Referring now to FIG. 4, in accordance with the present disclosure, first elongated member 14 may be formed of two panels comprising a first panel 42 and a second panel 46. The edges of the first and second panels 42, 46 are connected, such as by sewing, gluing, stapling, clamping, heat/ultra-sound (sonic) welding, or combinations thereof. First elongated member 14 includes a pocket, which defines an interior space 44 between first and second panels 42, 46.

First panel 42 comprises an outer surface 50 that preferably includes hook or loop structures. More preferably, outer surface 50 comprises hook structures and loop structures along first elongated member 14 between first end 30 and an opening 54 where second elongated member 18 is exposed between first panel 42 and second panel 46 of first elongated member 14. Thus, when first end 30 of first elongated member 14 runs through buckle 38, outer surface 50 may be formed into a loop by folding it against itself, thereby attaching the position of first elongated member 14 to buckle 38. By way of example and not limitation, first panel 42 may comprise a length of tape such as that sold under the trademark OMNI-TAPE® and manufactured by Velcro Industries B.V., Amsterdam, Netherlands, wherein the fastening surface comprises hook and loop structures on outer surface 50, as depicted in FIG. 4. The use of a combination of hook and loop structures on outer surface 50 of first elongated member 14 advantageously enables tourniquet 10 to be adjusted quickly when in use and able to accommodate a variety of sizes of limbs L, such as thighs and forearms.

To size the tourniquet 10 to limb L, the user simply wraps the tourniquet 10 around the subject limb L, loops the first end 30 of first elongated member 14 through the buckle 38, pulls the tourniquet 10 reasonably tight, and then presses the outer surface 50 together detachably interlocking the outer surface 50 of first elongated member 14 together with hook and loop structures within the region where the outer surface 50 overlaps beyond the buckle 38. Those skilled in the art will appreciate that the outer surface 50 of first elongated member 14 may be fitted with hook fasteners to match with corresponding loop fasteners. Although within the scope of the present disclosure, the ability of a tourniquet so modified to accommodate various sizes of limbs may be limited, nonetheless, such an issue could be addressed by manufacturing tourniquets of different sizes and providing tourniquets having different portions of the outer surface 50 fitted with various lengths of hook material to match-up with corresponding portions of loop material.

Alternatively, other means of fastening the overlapping portion of first elongated member 14 may be provided, such as with buttons, snaps, or transverse straps, and such variations and modifications are within the scope of the present disclosure.

It is further noted that although first elongated member 14 is preferably formed of a first panel 42 and a second panel 46, first elongated member 14 may be formed of a piece of material. By way of example, material may be folded and seamed to form a pocket or an interior space 44.

Referring to FIG. 4, second elongated member 18 is shown between the first panel 42 and the second panel 46 of first elongated member 14. In accordance with the present disclosure, second elongated member 18 comprises a length of nylon binding strap (also known as nylon binding tape) that extends from first end 30 of first elongated member 14 to the buckle 38 and returns to the first end 30 such that second elongated member 18 comprises a loop. Although a non-elastic, nylon, binding strap material is preferred for use as second elongated member 18, other elongated types of materials may be used, such as a section of rope, belt, tubing, hose, band, or combinations thereof, where such structures thereby form a means for compressing a body part. The ends of second elongated member 18 are preferably attached only at the tip 58 of the first end 30 of first elongated member 14, such as by sewing, gluing, stapling, clamping, heat/ultrasound (sonic) welding, or combinations thereof. Thus, second elongated member 18 can slide within the interior space 44 of first elongated member 14. Accordingly, second elongated member 18 comprises a material that has frictional characteristics, allowing it to slide within the interior space 44 of first elongated member 14 when a tensile force is applied to second elongated member 18. Although not required, depending upon the types of materials used to form first elongated member 14 and second elongated member 18, the interior space 44 of first elongated member 14 may optionally include a substance, such as a powder or other lubricant, to assist with the frictional characteristics between the surfaces of second elongated member 18 and the interior space 44 of first elongated member 14.

In accordance with the present disclosure, the tourniquet may comprise an inner strap 18 that extends through an end or a slit (not shown) at the first end 30, such as a slit in the first panel 42 of first elongated member 14. Second elongated member 18 may then be attached to the distal end of the second panel 46. Alternatively, a slit (not shown) may be formed in the second panel 46 and second elongated member 18 attached to the distal end of the first panel 42.

According to the present disclosure, the tourniquet 10 may be configured such that a layer (i.e., not a loop) of material is used to form second elongated member 18. Here, a first end of second elongated member 18 is attached at or near the tip 58 of the first end 30 of first elongated member 14, and a second end of second elongated member 18 is attached at or near buckle 38, with an intermediate portion not attached to first elongated member 14, thereby allowing second elongated member 18 to slide within first elongated member 14. The tension mechanism 22 can be used to tighten second elongated member 18, such as by winding a windlass 74 to develop tension in second elongated member 18. When rotated, windlass 74 produces a force with a linear component and a torsional component.

Referring to FIG. 4, in accordance with the present disclosure, tourniquet 10 preferably includes a base member 62. As by way of example and not limitation, base member 62 may be formed of a KYDEX® (Kieerdex Company, LLC, Mount Laurel, N.J.) thermoplastic or moldable (as for example, injection moldable) plastic. A first end 66 of base member 62 preferably includes a securing mechanism 26, as will be discussed below. Second panel 46 of first elongated member 14 extends over at least a portion of base member 62, passes through means for looping, such as buckle 38, and folds back to a second end 70 of base member 62. The edges of second panel 46 between buckle 38 and second end 70 of base member 62 are preferably connected, as for example, by sewing, gluing, stapling, clamping, or heat/ultra-sound (sonic) welding, thereby attaching second end 34 of first elongated member 14 to buckle 38.

Referring to FIG. 4, according to the present disclosure, second elongated member 18 emerges from first elongated member 14 at opening 54 where it is connected to tension mechanism 22. In FIG. 4, tension mechanism 22 comprises a windlass 74 that is shown in an unwound position. Windlass 74 comprises a plastic material; other types of materials are also within the scope of the disclosure. In accordance with the present disclosure, second elongated member 18 passes through a slot or an aperture 78 in windlass 74, and as described above, second elongated member 18 extends to and around buckle 38.

Figure 7:
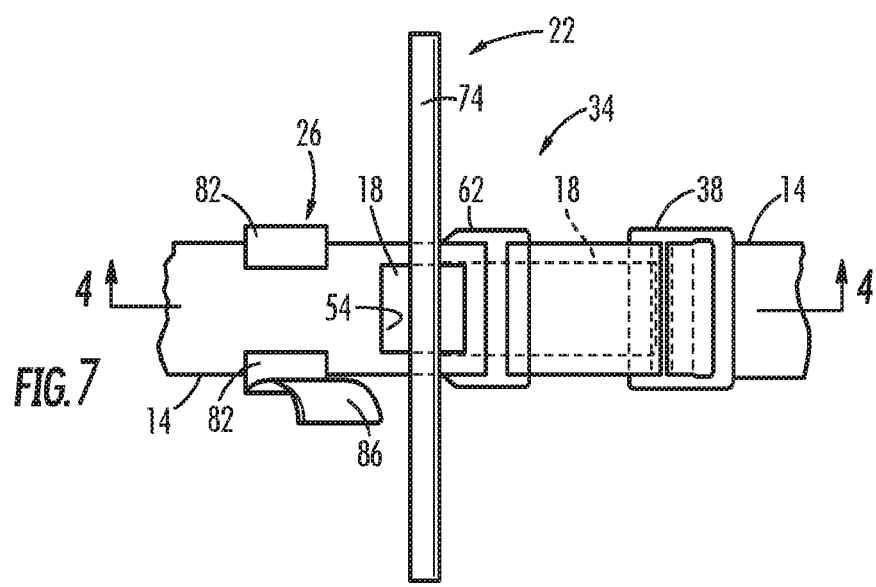
FIG. 7 is a plan view of the buckle end of the device with the first elongated member looped through the buckle and the windlass in an unwound position.

Referring to FIG. 7, a plan view of second end 34 of first elongated member 14 is shown. Here, first elongated member 14 is looped through buckle 38; tension mechanism 22, comprising windlass 74, as will be described below, is not shown wound to tighten second elongated member 18.

Figure 8:
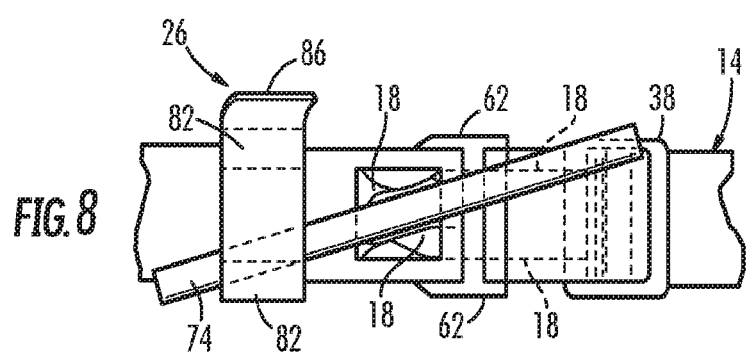
FIG. 8 is a plan view of the buckle end of the device with the first elongated member looped through the buckle and the windlass in a wound position.

Referring now to FIG. 8, a plan view of the second end 34 of first elongated member 14 is shown. Here, first elongated member 14 is run through buckle 38 to form a loop and windlass 74 has been partially wound, thereby applying a tensile force to second elongated member 18. Since the end of second elongated member 18 is attached to tip 58 of first elongated member 14, when windlass 74 is rotated, the intermediate portion of second elongated member 18 slides within first elongated member 14, essentially scrunching first elongated member 14 relative to second elongated member 18 as second elongated member 18 is increasingly tightened. The tightened second elongated member 18 provides even radial compressive pressure to limb L.

Referring now to FIG. 5, a cross-sectional view of tourniquet 10 is shown, including second end 34 of tourniquet 10 with windlass 74 in a partially wound position. More particularly, in use, after first end 30 of first elongated member 14 is run through buckle 38 and attached to limb L shown in FIG. 1, windlass 74 is rotated, such as in the direction of arrows A1 and A2, to apply a tensile force to at least a portion of second elongated member 18. Since second elongated member 18 is attached to a tip 58 of first end 30 of first elongated member 14, second elongated member 18 slides in the direction of arrows A3 and A4 within first elongated member 14 as windlass 74 is rotated, thereby pulling second elongated member 18 and providing a circumferentially applied compression force to limb L. The tensile force is primarily developed in the portion of second elongated member 18 between buckle 38 and windlass 74, with typically a lesser amount of tension developed in the overlapping portion of second elongated member 18 between buckle 38 and tip 58, because second elongated member 18 bends around buckle 38 after being applied to limb L, the bend tends to prevent the slippage of second elongated member 18 in the overlapped portion. After windlass 74 is tightened, tourniquet 10 restricts blood flow in limb L. Accordingly, tourniquet 10 of the present disclosure offers the advantage of an unlimited number of possible twists. More particularly, many prior art tourniquets are limited to a set number of twists by their windlasses, thus limiting the compression otherwise possible. As a result, such prior art tourniquets are venous tourniquets and are not suitable for arterial occlusion. The combination of first elongated member 14, inner strap 18, and tension mechanism 22 of the present disclosure overcome this prior art limitation.

Referring now to FIG. 6, a cross-sectional view of the second end 34 of tourniquet 10 is shown with windlass 74 in a wound position. In accordance with the present disclosure, after windlass 74 has been sufficiently tightened to restrict arterial blood flow in the appendage, windlass 74 may be secured using securing mechanism 26. The securing mechanism 26 provides a means for securing or preventing windlass 74 from unwinding. Thus, securing mechanism 26 maintains the wound position of windlass 74, and thereby maintains tension in second elongated member 18.

In accordance with the present disclosure, and as best seen in FIGS. 1, 7, and 8, securing mechanism 26 preferably comprises a pair of opposing hooked catches 82 set transverse to the longitudinal axis LA-LA of tourniquet 10.

More particularly, hooked catches 82 are preferably sized to cup or hold windlass 74, or a portion thereof, and prevent it from unwinding. Accordingly, hooked catches 82 are sufficiently stiff to provide adequate resistance against tensile force within second elongated member 18, as transferred to hooked catches 82 by windlass 74. In accordance with the present disclosure, and by way of example and not limitation, hooked catches 82 may be formed of a KYDEX® thermoplastic material or molded plastic that may be integrally formed with, or otherwise connected to, base member 62. Use of two opposing hooked catches 82 allows the user to rotate windlass 74 in either direction, with one of the two hooked catches 82 always able to prevent windlass 74 from unwinding. It is to be understood that use of a single hooked catch 82 may be used and is within the scope of the present disclosure. For hooked catch 82, the user rotates windlass 74 in the proper direction to allow tension in second elongated member 18 to be resisted by hooked catch 82 once winding of the windlass 74 and tensioning of second elongated member 18 is completed.

In accordance with the present disclosure, securing mechanism 26 may comprise a strap positioned transversely to a longitudinal axis LA-LA of first elongated member 14. As for example, a transversely oriented strap having hook and loop fastening portions or an elastic band engaging a hook or button may be provided to secure windlass 74 in its wound position.

In another alternative, a transversely oriented strap 86 may be used in combination with hooked catches 82. Such a combination of structures allows the user to secure windlass 74 and move about (or be moved by another person) with less concern of windlass 74 dislodging from hooked catches 82 and unwinding. In accordance with the present disclosure, for hooked catches 82 used in combination with a transversely oriented strap 86, the outer surface of hooked catches 82 may comprise a hook or loop material, and a surface of transversely oriented strap 86 may comprise a complementary hook or loop material to interlock with the material on hooked catches 82.

Figure 9:
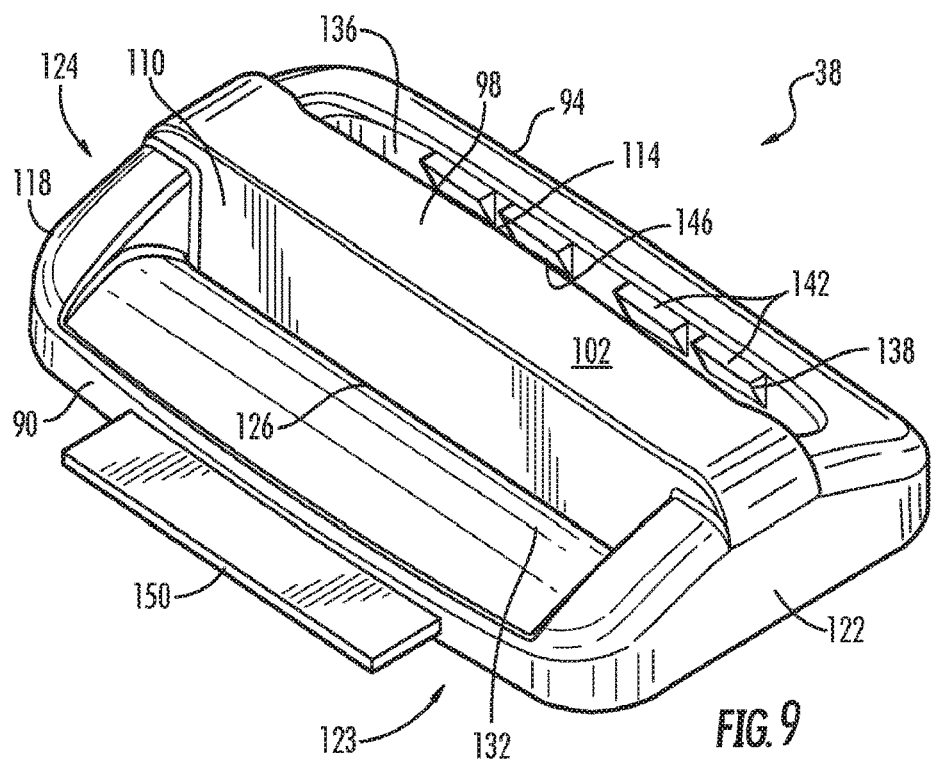
FIG. 9 is a top, front perspective view of a buckle of the device according to the present disclosure.
Figure 10:
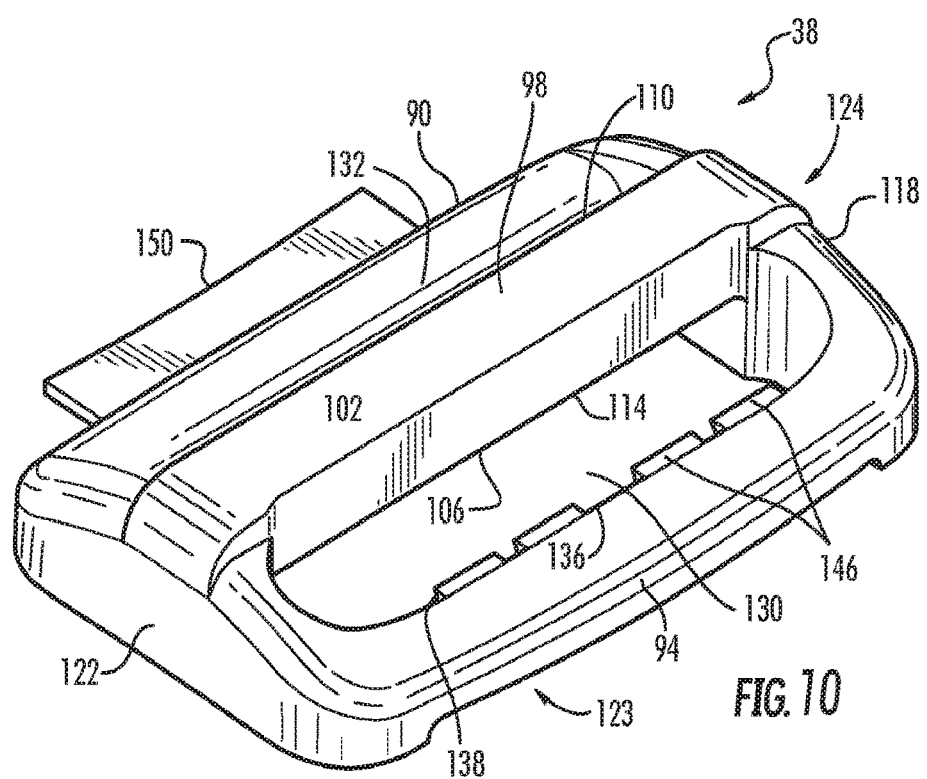
FIG. 10 is a top, rear perspective view of the buckle shown in FIG. 9.
Figure 11:
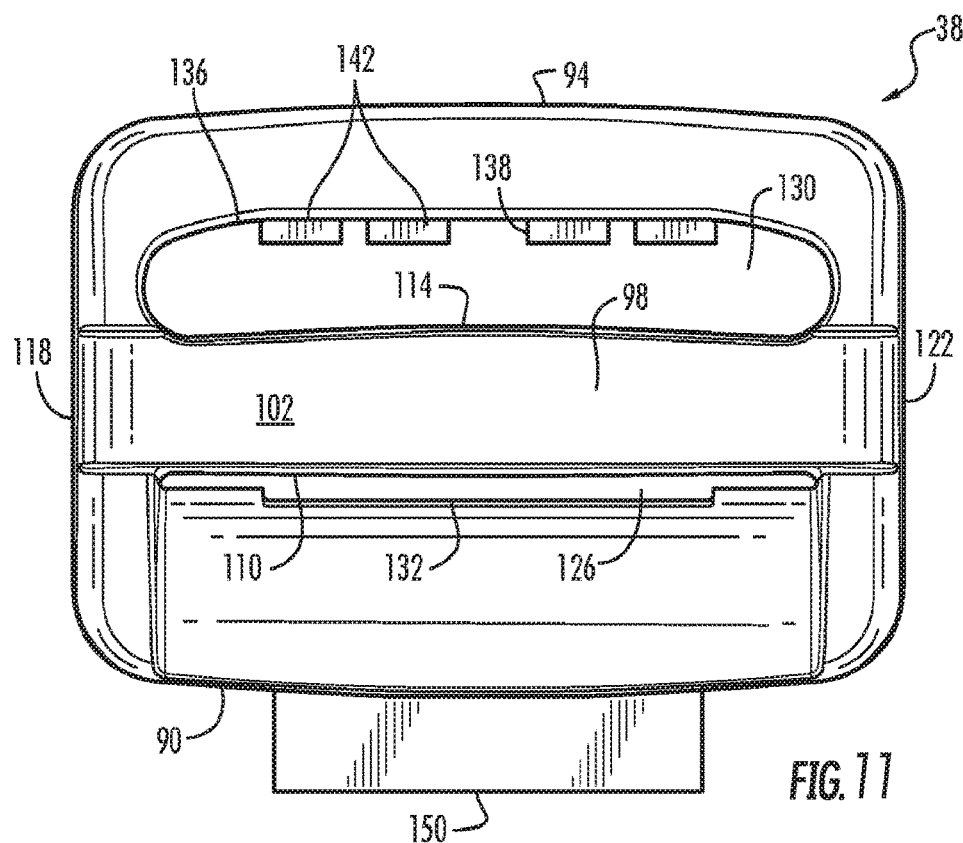
FIG. 11 is a plan view of the buckle shown in FIG. 9.

With reference to FIGS. 9-11, buckle 38 is shown for use in tourniquet 10. As previously described, first end 30 of first elongated member 14 is looped through buckle 38 and pulled tight around limb L to allow first elongated member 14 to circumferentially surround or encircle limb L. More specifically, buckle 38 includes a first lateral side 90, a second lateral side 94, and an intermediate bar 98 generally parallel to and located between first lateral side 90 and second lateral side 94. Intermediate bar 98 includes a top surface 102, a bottom surface 106, a first intermediate sidewall 110, and a second intermediate sidewall 114 located between top surface 102 and bottom surface 106. A first end 118 and a second end 122 of buckle 38 interconnect first lateral side 90, second lateral side 94, and intermediate bar 98. First lateral side 90 includes a first lateral sidewall 132 and an anti-torsion plate 150, and second lateral side 94 includes a second lateral sidewall 136. Located between first lateral side 90 and intermediate bar 98 is a first port 126, and formed between second lateral side 94 and intermediate bar 98 is a second port 130. Each port provides a route or pathway for looping first elongated member 14 through buckle 38 during tightening and loosening of first elongated member 14 around limb L shown in FIG. 1. Buckle 38 is preferably constructed of a polymer, such as plastic or rubber, it is also contemplated that buckle 38 could be constructed of other materials, such as metals or composites.

Figure 12:
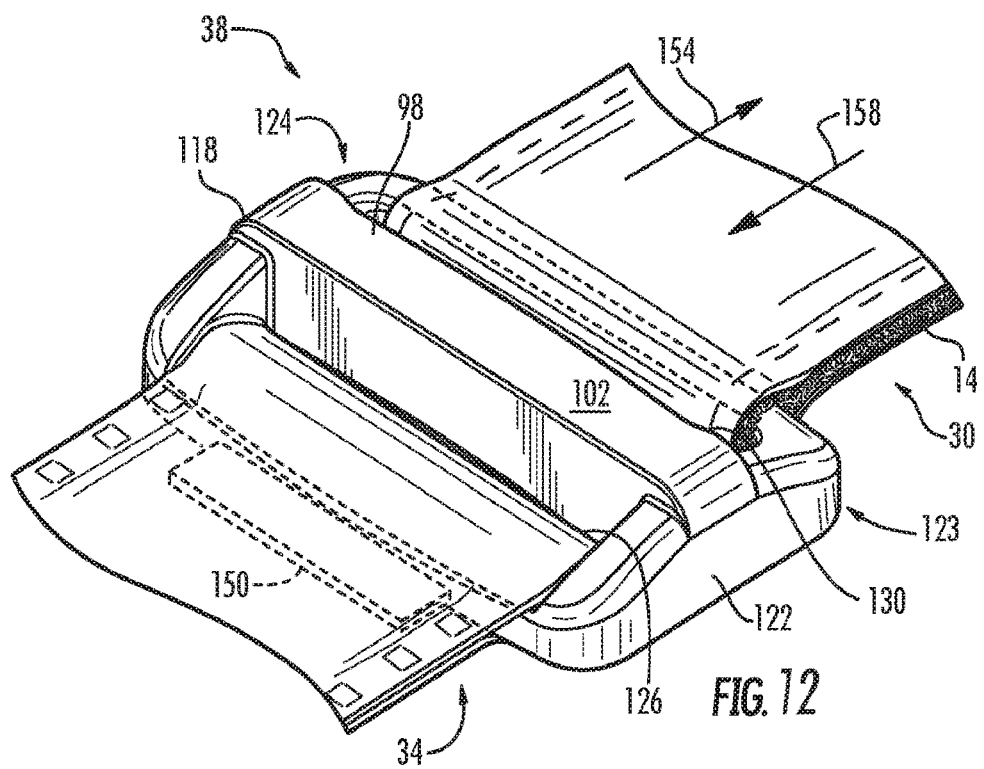
FIG. 12 is a top, front perspective view of the buckle shown in FIG. 9, showing the first end of the first elongated member being looped through the second port of the buckle.
Figure 13:
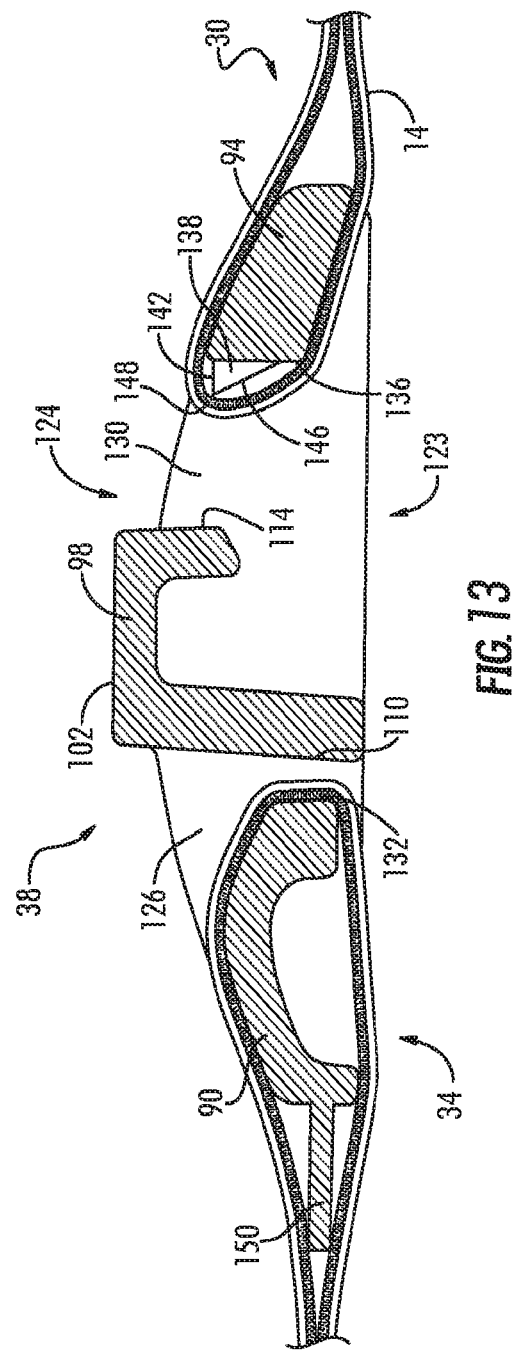
FIG. 13 is a cross-sectional view of a portion of the buckle shown in FIG. 9, illustrating the interaction of the first elongated member with the anti-torsion plate and the tooth set.

Referring now to FIGS. 12 and 13, second end 34 of first elongated member 14 is fed through first port 126, from top 124 to bottom 123 of buckle 38. Second end 34 of first elongated member 14 is preferably attached to the remainder of first elongated member 14 by sewing, gluing, stapling, clamping, heat/ultra-sound (sonic) welding, or a combination thereof, thereby attaching second end 34 of first elongated member 14 to buckle 38.

With respect to FIGS. 9-13, anti-torsion plate 150 is shown extending horizontally from first lateral side 90. During operation, anti-torsion plate 150 provides resistance at buckle 38 against a torsional force transferred by windlass 74 of the tension mechanism 22 to second elongated member 18. With reference to FIG. 1, the resistance at buckle 38 prevents the torsional force transferred by the windlass 74 to second elongated member 18 from twisting buckle 38, thereby reducing the likelihood of the buckle 38 pinching the Limb L during operation.

Referring now to FIGS. 9, 12 and 13, second port 130 includes a tooth set 138 mounted to second lateral sidewall 136 for inhibiting movement of first elongated member 14 with respect to buckle 38. Tooth set 138 comprises at least one tooth. With reference to FIG. 13, each tooth includes a top surface 142, an inclined surface 146, and an edge or projection 148 therebetween. During operation and with respect to FIG. 12, first end 30 of first elongated member 14 is fed through second port 130 from bottom 123 to top 124 of buckle 38. After first end 30 has exited second port 130 and been pulled to tightness around limb L, the hook and loop fastener on outer surface 50 of first end 30 of first elongated member 14 is mated with the hook and loop fastener on bottom surface 50 of the remainder of first elongated member 14 in order to attach first elongated member 14 around the appendage.

Referring now to FIG. 13, a more detailed view illustrating the interaction between tooth set 138 and first elongated member 14 is shown. More specifically, once first end 30 of first elongated member 14 has been fed through second port 130, projections 148 of tooth set 138 engage with the hooks and loops on outer surface 50 of first elongated member 14.

Increased drag on first elongated member 14, provides resistance to the free movement of first elongated member 14 relative to the buckle 38. Drag is especially useful in situations when the hook and loop fastener on the bottom surface of first end 30 of first elongated member 14 accidentally detaches from the hook and loop fastener on outer surface 50 of the remainder of first elongated member 14. Thus, the one or more teeth provide an extra safety mechanism to prevent inadvertent disengagement of first end 30 of first elongated member 14 from buckle 38 when, for instance, a patient utilizing tourniquet 10 is moved, dragged, crawls, etc. Further, those of ordinary skill in the art will appreciate how the inclined surface 146 of the tooth set 138 facilitates movement of first elongated member 14 in a tightening direction of travel 154.

Referring to FIG. 13, the arrangement of tooth set 138 on buckle 38 is advantageous to simplify the manufacturing of buckle 38 in addition to facilitating the tightening movement of first elongated member 14 within buckle 38. While tooth set 138 is illustrated as being situated in second port 130, ordinary artisans will appreciate that there can be one or more than one tooth set and that they can be situated in either first port 126 or second port 130 or both first port 126 and second port 130. Additionally, it will be appreciated that one tooth set can be inverted while the other is not, or both tooth sets can be inverted or not inverted, in order to satisfy specific functional preferences regarding the facilitation of or drag to the movement of first elongated member 14 when interacting with the overall surface of the tooth set(s). Regarding the various possible tooth set arrangements, it will further be appreciated that first end 30 of first elongated member 14 can be fed through first port 126 from bottom 123 to top 124 of buckle 38, over intermediate bar 98, and then through second port 130 from top 124 to bottom 123 of buckle 38. Relevant considerations in determining which features to incorporate in buckle 38 may include ease and cost of manufacturing, ease of assembly of first elongated member 14 and buckle 38, familiarity of the operators with buckle 38, and an amount of drag applied to first elongated member 14, among others.

Further, while four teeth are shown in tooth set 138, it is contemplated that fewer teeth (including a single tooth) may be provided to facilitate manufacturing, to provide for fewer sharp edges, or for other reasons that an operator may desire. Additionally, more than four teeth may be provided to increase the gripping ability of tooth set 138. Further, while each tooth is shown to be of a triangular profile, teeth of other shapes are within the scope of the present disclosure, such as bulbous-shaped teeth, teeth having sharp points, or teeth having two inclined surfaces, among others. Also, the angle of any inclined surfaces can be modified in order to provide more or less drag on first elongated member 14.

Many modifications and substitutions will come to mind to one skilled in the art to which this disclosure pertains having the benefit of the teachings presented in the foregoing descriptions and the associated drawings. Therefore, it is to be understood that the disclosure is not to be limited to the specific examples provided and that modifications and substitutions are intended to be included within the scope of the appended claims. Although specific terms are employed herein, they are used in a generic and descriptive sense only and not for purposes of limitation. In addition, where possible, any terms expressed in the singular form herein are meant to also include the plural form and/or vice versa. As used herein, "at least one" shall mean "one or more" and these phrases are intended to be interchangeable. Accordingly, the terms "a" and/or "an" shall mean "at least one" or "one or more," even though the phrase "one or more" or "at least one" is also used herein.

What is claimed is:
1. A tourniquet, comprising:
   (a) a first elongated member having a first end and a second end;
   (b) a second elongated member having a first end and a second end, wherein said first end of said second elongated member and said second end of said second elongated member are attached to said second end of said first elongated member with an intermediate portion of said second elongated member between said first end of said second elongated member and said second end of said second elongated member, said second elongated member being slidable with respect to said first elongated member;
   (c) a windlass operable to apply a force to said intermediate portion, said force having a lineal component and a torsional component;
   (d) a buckle having
      (1) a first lateral side with a first outer lateral sidewall and a first inner lateral sidewall,
      (2) an anti-torsion plate attached to said first outer lateral sidewall,
      (3) a second lateral side; and
      (4) an intermediate bar located between said first lateral side and said second lateral side, wherein said second end of said first elongated member is dimensioned to be inserted between said first lateral side and said intermediate bar to define a loop, and said anti-torsion plate resists said torsional component of said force on said intermediate portion when said force is applied to said intermediate portion by said windlass.
2. The tourniquet of claim 1, wherein said anti-torsion plate has a side, and wherein said loop in said second end of said first elongated member encircles said anti-torsion plate.
3. The tourniquet of claim 1, wherein said anti-torsion plate is rectangular and has a first side, a second side and a third side, said first side of said rectangle being attached to said first lateral sidewall of said first lateral side, and wherein said loop is attached along a second side and a third side of said anti-torsion plate.
4. The tourniquet of claim 1, further comprising a base, said first elongated member attached to said base and operable, when said windlass applies a force to said second elongated member, to draw said first end of said second elongated member and said second end of said second elongated member toward said base.
5. The tourniquet of claim 1, wherein said second lateral side of said buckle has at least one tooth.
6. The tourniquet of claim 1, wherein said second lateral side of said buckle has four teeth.
7. The tourniquet of claim 1, wherein said second lateral side of said buckle has at least one tooth extending toward said intermediate bar.
8. A tourniquet, comprising:
   (a) a first elongated member having a first end and an opposing second end;
   (b) a windlass operatively connected to said first elongated member and operable to apply a force to said first elongated member, said force having a linear component and a torsional component;
   (c) a buckle having
      (1) a first lateral side with a first outer lateral sidewall and a first inner lateral sidewall,
      (2) an anti-torsion plate attached to said first outer lateral sidewall,
      (3) a second lateral side; and
      (4) an intermediate bar located between said first lateral side and said second lateral side, wherein said second end of said first elongated member is dimensioned to pass between said first lateral side and said intermediate bar of said buckle to define a loop, said anti-torsion plate resisting said torsional component of said force on said loop when said force is applied by said windlass.
9. The tourniquet of claim 8, wherein said second lateral side of said buckle has at least one tooth.
10. The tourniquet of claim 8, wherein said second lateral side of said buckle has four teeth.
11. The tourniquet of claim 8, wherein said second lateral side of said buckle has at least one tooth extending toward said intermediate bar.
12. A tourniquet, comprising:
   (a) a first elongated member having a first end and an opposing second end;
   (b) a second elongated member having a first end and a second end, wherein said first end of said second elongated member and said second end of said second elongated member are attached to said second end of said first elongated member with an intermediate portion of said second elongated member between said first end of said second elongated member and said second end of said second elongated member being slidable with respect to said first elongated member;
   (c) a windlass operable to apply force to said intermediate portion, said force having a lineal component and a torsional component;
   (d) a buckle having
      (1) a first lateral side with a first outer lateral sidewall and a first inner lateral sidewall,
      (2) a second lateral side; and
      (3) an intermediate bar located between said first lateral side and said second lateral side, wherein said second end of said first elongated member is dimensioned to fit between said first lateral side and said intermediate bar; and

(e) an anti-torsion plate attached to said first outer lateral sidewall of said buckle, said anti-torsion plate resisting said torsional component of said force on said intermediate portion of said second elongated member when said force is applied to said intermediate portion by said windlass.

13. The tourniquet of claim 12, wherein said anti-torsion plate is a rectangle.

14. The tourniquet of claim 12, wherein said anti-torsion plate is covered by said first end of said first elongated member.

15. The tourniquet of claim 12, wherein said anti-torsion plate is held within said first elongated member.

* * * * *